(12) United States Patent
Bystritsky

(10) Patent No.: US 7,283,861 B2
(45) Date of Patent: Oct. 16, 2007

(54) METHODS FOR MODIFYING ELECTRICAL CURRENTS IN NEURONAL CIRCUITS

(76) Inventor: Alexander Bystritsky, 613 N. Foothill Rd., Beverly Hills, CA (US) 90210

( * ) Notice: Subject to any disclaimer, the term of this patent is extended or adjusted under 35 U.S.C. 154(b) by 336 days.

(21) Appl. No.: 10/135,137

(22) Filed: Apr. 30, 2002

(65) Prior Publication Data

US 2003/0204135 A1 Oct. 30, 2003

(51) Int. Cl.
*A61N 7/00* (2006.01)
(52) U.S. Cl. .................... 600/411; 600/427; 600/436; 600/544; 601/2
(58) Field of Classification Search ............ 600/407, 600/411, 427, 436, 544; 601/2
See application file for complete search history.

(56) References Cited

U.S. PATENT DOCUMENTS

| | | | |
|---|---|---|---|
| 4,343,301 A | 8/1982 | Indech | 128/24 |
| 5,247,935 A | 9/1993 | Cline | 128/653.2 |
| 5,275,165 A | 1/1994 | Ettinger | 128/653.2 |
| 5,291,890 A | 3/1994 | Cline | 128/653.2 |
| 5,323,779 A | 6/1994 | Hardy | 128/653.2 |
| 5,476,438 A | 12/1995 | Edrich | 600/2 |
| 5,738,625 A * | 4/1998 | Gluck | 600/9 |
| 6,094,598 A * | 7/2000 | Elsberry et al. | 607/116 |
| 6,198,956 B1 | 3/2001 | Dunne | 600/407 |
| 6,198,958 B1 | 3/2001 | Ives et al. | 600/411 |
| 6,267,734 B1 | 7/2001 | Ishibashi | 601/2 |
| 6,612,988 B2 * | 9/2003 | Maor et al. | 600/439 |
| 6,708,051 B1 * | 3/2004 | Durousseau | 600/383 |
| 2002/0173697 A1 * | 11/2002 | Lenhardt | 600/25 |
| 2004/0048795 A1 * | 3/2004 | Ivanova et al. | 514/12 |

OTHER PUBLICATIONS

Roth et al., "Deep Brain Stimulation in Neuropsychiatric Disorders", Current Psychiatry Report (Oct. 2001), vol. 3, No. 5, pp. 366-372.
Barlow et al., "The Risk of Seizures after Receipt of Whole-Cell Pertussis or Measles, Mumps, and Rubella Vaccine", New England Journal of Medicine (Aug. 30, 2001), vol. 345, No. 9, pp. 656-661.
George et al., "Transcranial Magnetic Stimulation: A Neuropsychiatric Tool for the 21$^{st}$ Century", Journal of Neuropsychiatry and Clinical Neuroscience (fall 1996), vol. 8, No. 4, pp. 373-382.
Clement et al., "A hemispher array for non-invasive brain therapy and surgery", Physics in Medicine & Biology, (Dec. 2000), vol. 45, No. 12, pp. 3707-3719.
Rauch et al., "Clinical Neuroimaging in Psychiatry", Harvard Review of Psychiatry (Mar./Apr. 1995) vol. 2, No. 6, pp. 297-312.

\* cited by examiner

*Primary Examiner*—Ruth S. Smith
(74) *Attorney, Agent, or Firm*—Pillsbury Winthrop Shaw Pittman LLP

(57) ABSTRACT

Disclosed herein are methods for modifying electrical currents in brain circuits through the simultaneous use of focused ultrasound pulse (FUP) and an existing brain-imaging system, such as a functional magnetic resonance imaging (fMRI) system. The methods are used for research, treatment and diagnosis of psychiatric, neurological, and neuroendocrine disorders whose biological mechanisms include brain circuits. The methods include the simultaneous steps of applying FUP to a live neuronal circuit within a brain and monitoring a brain image produced by a brain imaging system during the application of FUP.

36 Claims, 3 Drawing Sheets

METHODS FOR MODIFYING ELECTRICAL CURRENTS IN NEURONAL CIRCUITS

BACKGROUND OF THE INVENTION

1. Field of the Invention

The present invention relates to methods for medical diagnosis and treatment, and more particularly to methods for diagnosis and treatment of specific psychiatric, neurological and neuroendocrine conditions using a Focused Ultrasonic Pulse (FUP) delivered to different points of neuronal circuits within the brain using existing focused ultrasound devices. The treatment is performed under the guidance of the existing brain-imaging devices, such as functional magnetic resonance imaging (fMRI).

2. Brief Description of the Prior Art

With advances in brain imaging techniques, the pathophysiology of psychiatric and medical disorders began to be more and more related to the specific neuronal circuits. Neuronal circuits are specific brain centers functionally and anatomically connected with each other. Usually a circuit involves sub-cortical neuronal centers connected with cortex. It is not totally clear how the circuits operate. However, it is clear that they play a major role in multiple psychiatric, neurological and medical conditions. For example, Obsessive Compulsive Disorder (OCD) and OCD Spectrum Disorders including Impulse Control Disorders appear to be related to abnormality in Orbito-Fronto-Talamic-Striatum circuit. Panic Disorder, Social Anxiety Disorder and panic spectrum disorders seem to be associated with the abnormal functioning of circuit involving Orbital-Frontal cortex, Amygdala, Cingulum and Hippocampus. Post-Traumatic Stress Disorders seem to associate with Prefrontal Cortex, Amydgala and Hippocampus abnormalities. Psychotic disorders seem to have an association with Prefrontal Cortex-Talamic-Striatum and Occipital Cortex Circuits. Circuits involved in neurological conditions have also been identified. For example, Parkinsonian Disease, Huntington Chorea, La Touretts and tick syndromes seem to have abnormalities in Cortico-Talamic-Straitum Circuit. Chronic pain has association with cortico-thalamic circuits. Insomnia has association with temporal cortex-lymbic-cingulum circuit. Medical conditions seem to have connection with specific neurocircuitry. For example, obesity and stress are associated with temporal-hypothalamic circuit. For a simple review and description of the above circuits, see Clark, D. L. and Boutros, N. N., *Brain and Behavior* (1999) and Rauch, S. L. et al., "Clinical Neuroimaging in Psychiatry" in *Harvard Review of Psychiatry* (1995), Vol. 2, no. 6, pp. 297-312.

Neuroimaging techniques exist that permit assessment of rapid changes in activity of the brain. Functional Nuclear Magnetic Resonance (fMRI), Vector Electroencephalagraphy (V-EEG) and Positron Emission Tomography (PET) are the most promising. These techniques, specifically fMRI, are capable of producing real time 3-dimensional maps of brain activity. These techniques merit scientists to study the neuronal circuits involved in pathology of different psychiatric or neurological conditions. However, the study process has been slowed by the absence of reliable activation of these circuits.

Recently, a few novel methods of the treatment of mental and neurological disorders directed at neuronal circuits have been introduced. These include deep brain stimulation by implanted electrodes, successfully used in OCD, Parkinson's disease and epilepsy, and brain surgery used in the treatment of OCD and depression. See *New England Journal of Medicine* (Sep. 27, 2001), pp. 656-63; R. M. Roth, et al., *Current Psychiatry Report* (October 2001), Vol. 3, no. 5, pp. 366-72. Because of the invasiveness and possible complications, these methods are reserved for the treatment resistant conditions where other treatments fail. However, the success of these treatments underlines the importance of specific neurocircuits in the pathophysiology of mental and neurological disorders. Furthermore, it underlines the importance of developing noninvasive methods of intervention at the neuronal circuit level. In addition, the studies using deep brain stimulation techniques determined that low frequency (2-150 Hz) signals inhibit the neuronal tissue and that high frequency (1-3 MHz) signals stimulate neuronal circuits.

Recently it has been proposed that neuronal circuits can be assessed and modified non-invasively using Transcranial Magnetic Stimulation (TMS). The signal from the brain after the TMS stimulation can be read using MRI. That method has been described in U.S. Patent No. 6,198,958, incorporated herein by reference, which described using the method for therapeutic purposes. The method and device proposed by that patent are currently being implemented in psychiatry and neurology for diagnostic and therapeutic purposes. See M.S. George, et al., *Journal of Neuropsychiatry and Clinical Neuroscience* (Fall 1996), Vol. 8, no. 4, pp. 373-382. The method, however, has several problems. For example, TMS does not stimulate deep brain centers, because it is incapable of penetrating brain tissue deeper than 1-2 cm. Also, TMS has a large area of focus, 1 cubic cm or more, which does not permit focused activation of a specific neuronal circuit. Also, there is a problem in using TMS together with fMRI, because TMS produces a magnetic signal that interferes with the magnetic field and consequently with the fMRI image.

Focused ultrasound has been used to modify electrical currents in neuronal tissue. This has been done by a combined application of a magnetic field and an ultrasonic field to neuronal and other tissue in the body. The prior art proposes that modification of electrical currents in neuronal tissue will come from the interaction of the two fields. For example, U.S. Pat. No. 4,343,301 describes generating high energy by intersecting two ultrasound beams within any single fixed point of the body, including the skull. While it is not proven that such an application of ultrasound would do anything except heat or destroy tissue, there is recent evidence that application of focused ultrasound to brain slices, subjected to simultaneous electrical stimulation, can change the electrical currents in the slices. However, because two ultrasound beams cannot be focused within the skull, because of the complexity of bone density and bone structure, it is not possible to focus such a two-beam device in the brain tissue.

Some companies have produced ultrasonic devices that use multiple beams. See G. T. Clement, et al., *Physics in Medicine and Biology* (December 2000), Vol. 45, no. 12, pp. 3707-3719. By coordinating the amplitude and the phase of the ultrasound beams generated by multiple sources via computer multi-beam devices, algorithms can be developed to adjust the bone dispersion of the beam and focus the ultrasound within the brain tissue. These devices are to be used as ultrasonic knives within the brain for the destruction of tumors, for example. However, they cannot be used to modify the electrical and electromagnetic currents within the brain circuits without harming the surrounding tissue.

SUMMARY OF THE INVENTION

It is an object of the invention to provide methods for stimulating neurons within the brain of a mammal, preferably a human, by modifying electrical currents in a live neuronal circuit. The modification is accomplished by applying a focused ultrasound pulse (FUP) under the guidance of a brain-imaging system such as a functional magnetic resonance imaging (fMRI) system, a vector-electroencephalograph (V-EEG), or a positron emission tomograph (PET), preferably fMRI. The application of FUP is generally via multiple ultrasound transducers that are housed in a cap worn by a patient. It is simultaneous with the use of the brain-imaging system. The application of different frequencies and phases of FUP to the brain circuits will generate a signal that will be captured by fMRI. At that time, changes in circuits will be assessed. This will permit adjustment of the focus of the FUP and of the location of the FUP, or the use of multiple focuses, to achieve the maximum modification of the circuit. The changes in the circuit are useful for research, diagnosis and treatment.

It is a further object of the methods to diagnose and treat specific psychiatric, neurological, and neuroendocrine conditions. Examples of such conditions include, but are not limited to, Obsessive Compulsive Disorder and its spectrum, Post Traumatic Stress Disorder, Depression, Bipolar Disorder, Social Anxiety Disorder, Psychotic Disorders, Panic Disorder, Ticks, Chronic Pain Syndrome, Insomnia, Chronic Fatigue Syndrome, Insomnia, Stress and Obesity, and other conditions apparent to one of ordinary skill in the art.

BRIEF DESCRIPTION OF THE DRAWINGS

A detailed description of embodiments of the invention will be made with reference to the accompanying drawings, wherein numerals designate corresponding parts in the several figures.

DETAILED DESCRIPTION

Figure 1:
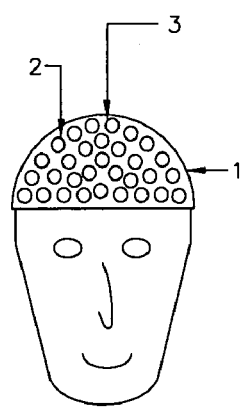
FIG. 1 illustrates an FUP device according to one embodiment of the invention. Show is a modified multi-transducer cap, capable of focusing ultrasound in the skull and delivering the FUP signal to a specific target in the brain.

FIG. 1 illustrates a preferred embodiment of a focused ultrasound pulse (FUP) device. A cap 1 houses multiple ultrasound transducers 2, preferably 300-1000 transducers. The FUP device is preferably a multi-beam ultrasonic device, which is coordinated via computer with conventional brain-imaging system, such as a focused magnetic resonance imaging (fMRI) system, a vector-electroencephalograph (V-EEG) or a positron emission tomograph (PET), preferably an fMRI system. An example of a preferable multi-beam ultrasonic device is an ultrasound knife. The transducers are regulated via a computer capable of focusing the ultrasound waves into a specific point 3. The cap and transducers are preferably made from a non-ferromagnetic material, a material that has a very low permeability and residual magnetism and hysterisis, such as copper. The use of a non-ferromagnetic material reduces fMRI field distortion and thereby reduces distortion of the image, permitting the application of FUP concurrently with the use of fMRI. By concurrent, it is meant that one applies an FUP within 1 millisecond to 10 seconds before or after using the fMRI system to image the brain.

Figure 2:
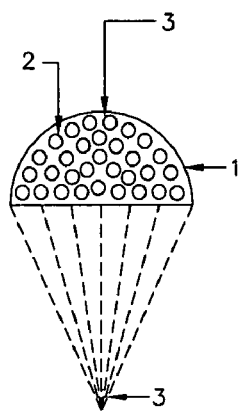
FIG. 2 illustrates how the cap of FIG. 1 can be placed on the head of a human subject.

FIG. 2 illustrates how the cap can be placed on the head of a human subject. A computer, which is coupled to the FUP device, controls the parameters of the FUP, including focus, frequency, phase and amplitude. Through user interaction with the computer, the FUP device is capable of producing a focused ultrasound pulse in a specific point within the brain. The FUP's focus is preferably 2 or more centimeters deep and 0.5-1000 mm in diameter, and more preferably 2-12 cm deep and 0.5-2 mm in diameter. The specific point is determined by a conventional brain-imaging system, preferably an fMRI system, which provides information about brain form and density. FUP software is preferably coordinated with fMRI software for precise positioning and coordination of the focused signal. The changes in activity within the neuronal circuits are determined by monitoring the changes in the brain image produced by the fMRI before the application of FUP and during and after the application of FUP. These changes are used to determine exactly where the FUP focus was in the brain and the functional connectivity between the focus and surrounding brain centers. The specific point may be confirmed using the addition of a computed tomography (CT) scan, which provides information about bone density and structure of the skull and brain. The focus of the FUP may then be modified to direct it into a different point of the brain.

A single FUP may be applied to a single live neuronal circuit. Multiple FUPs may be applied to the same live neuronal circuit. Additionally, a single FUP may be applied to multiple live neuronal circuits, and multiple FUPs may be applied to multiple live neuronal circuits.

FUP given in different frequency, phase and amplitude will produce different effects on neuronal circuits and centers. Low frequencies, below 300 Hz, will decrease the firing of the centers and inhibit or disrupt the neuronal circuits. High frequencies, 500 Hz to 5 MHz, will produce activation of firing of neuronal centers and activation of the circuits. In either case, the FUP will modify physiological properties in the circuits. This will happen both when the FUP is applied to the centers and when the FUP is applied to the white matter.

Repeated application of the FUP to neuronal circuits will cause long-term or permanent changes to the circuits. The modification of the circuits using FUP will be used for the treatment of psychiatric, neurological and neuroendocrine disorders. Examples of such diseases include, but are not limited to, Obsessive Compulsive Disorder (and its spectrum), Post Traumatic Stress Disorder, Depression, Bipolar Disorder, Social Anxiety Disorder, Psychotic Disorders, Panic Disorder, Ticks, Chronic Pain Syndrome, Insomnia, Chronic Fatigue Syndrome, Insomnia, Stress, Obesity, and other conditions apparent to one of ordinary skill in the art. This will be done by repeated assessment and modification of changes in neuronal flow or field activity under the guidance of specific brain imaging techniques, such as fMRI, V-EEG, or PET.

Figure 3:
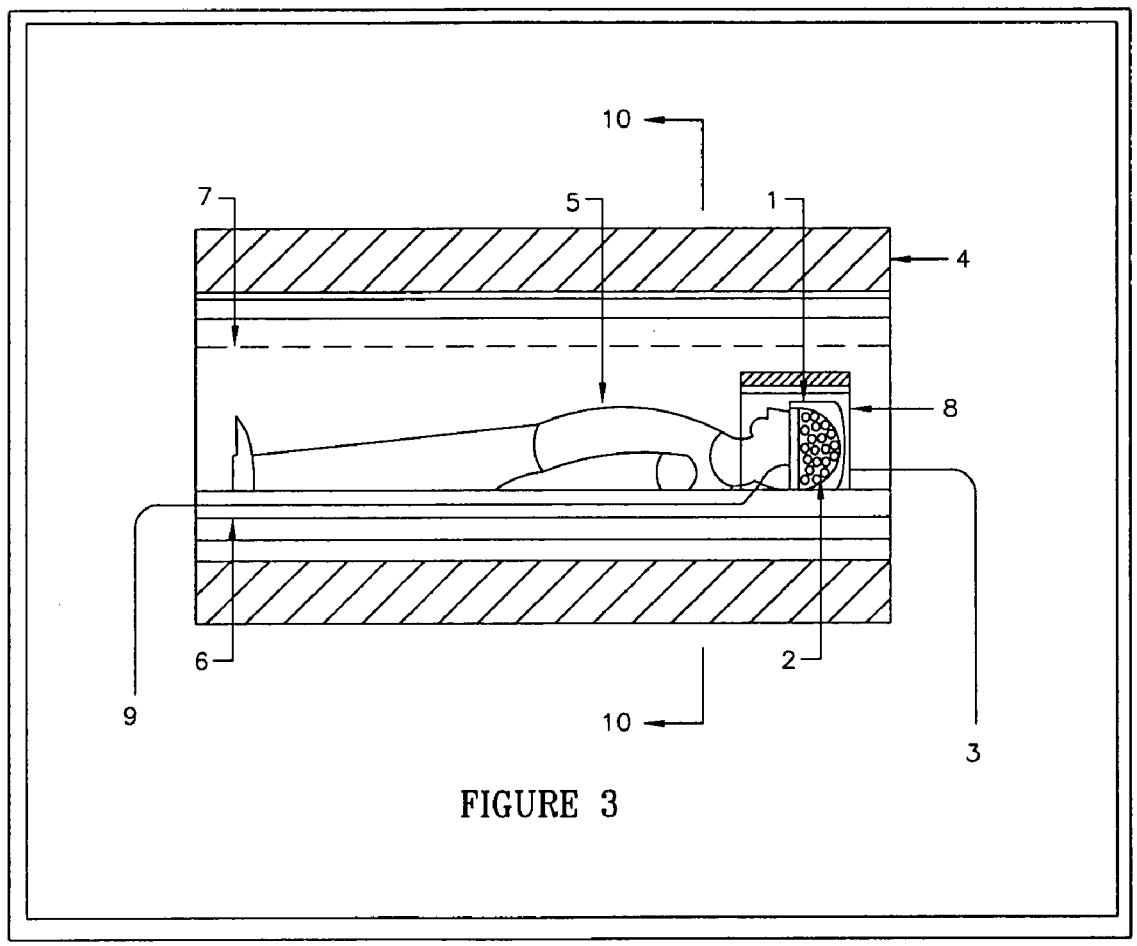
FIG. 3 illustrates a system in accordance with the present invention in which the FUP device is being used in conjunction with the brain imaging system, here shown as fMRI.

FIG. 3 illustrates the FUP being used in conjunction with a fMRI system. The fMRI system is preferably a typical GE build cylindrical magnet 4. The patient 5 preferably lies on a sliding platform 6 inside of the magnetic cavity 7. The imaging coil 8, which has been placed over the head of the patient, detects the magnetic resonance field generated by rotation of the magnet 4. The field signals detected by the imaging coil are preferably transmitted to the processing electronics outside the magnet. As a result of the fMRI system's computer analysis, a functional image of the brain is generated.

Figure 4:
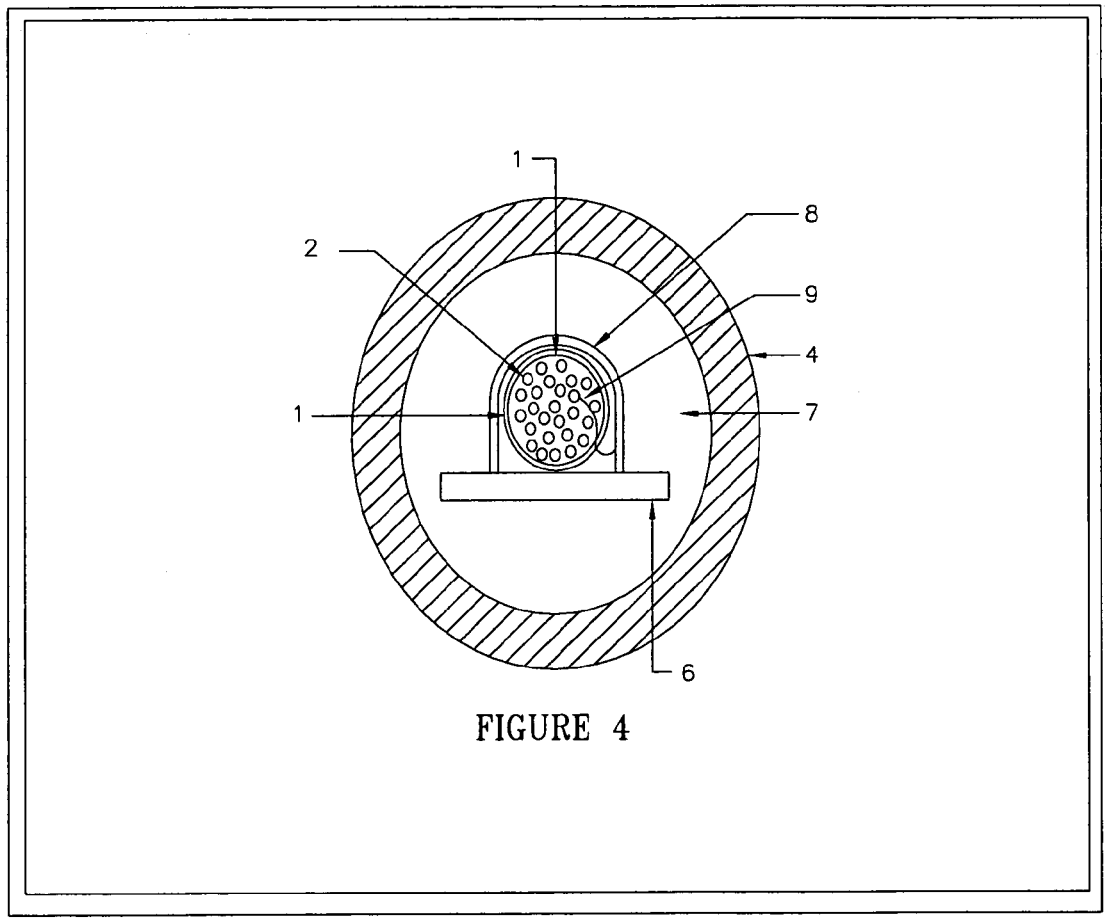
FIG. 4 illustrates a perspective of the right side of the system shown in FIG. 3, looking down on the head of the human subject.

FIG. 4 illustrates a cross-sectional view of FIG. 3, from a perspective looking down on the head of the patient, as shown by reference numeral 10 in FIG. 3. The cap 1 containing the FUP transducers 2 is preferably on the head of the patient. The imaging coil 8 is preferably placed above the FUP cap. A cable 9 connects the FUP cap with the transducers to the computer, which is kept outside of the room, controlling the FUP. The FUP device is also connected to MRI processing electronics. The FUP device generates FUP pulses that cause activation or deactivation of specific neuronal centers or circuits. The fMRI signal is modified in specific locations. This modification is captured and used to adjust the FUP transducers to achieve better focus, different position, or different influence on the neuronal circuit by modification of the frequency of the waves, frequency of the pulse, intensity of the pulse, or the phase of the waves.

The use of FUP in combination with fMRI or other imaging devices can provide a variety of diagnostic, research and therapeutic benefits. The invention can be used to create a functional map of the brain in response to modification of the neuronal circuits. It can also allow one to observe the functional connectivity within the brain of normal subjects as well as in the brain of the subjects suffering from various neurological conditions (such as the ones identified above). The invention can also be used treat these conditions, and may be used concurrently with the pharmaceutical agents commonly prescribed for them.

Development of the functional brain maps can significantly improve our understanding of the operation of the brain in normal subjects and in different diseased states. Unlike the use of transcranial magnetic stimulation (TMS), which can only read a brain tissue depth of 1-2 cm, the FUP is able to reach brain tissue much deeper, 2 or more centimeters into the brain, for example 2-12 cm. The FUP can also produce a focus of energy that will be only 0.5-2 mm. in diameter, as opposed to 2-3 cm. attainable by TMS.

The invention can be used for evaluation of the outcome of a variety of treatments. For example, the functional maps of the brain, such as those mapping functions of different areas of the brain after application of the FUP, could be constructed using fMRI before and after a particular treatment. If after the treatment the functional reactivity of a certain neuronal circuit becomes similar to that of normal controls that may be an indicator of the efficacy of a treatment. In the same way, the invention can be used to determine when the activity of the certain neuronal areas reaches a specific level. Also, the repeated application of FUP may modify the circuits in such a way that their functionality becomes the same as in normal subjects. Repeated application together with continuous fMRI monitoring may help us to determine the most efficient, reliable and fast ways to achieve the normalization of neuronal structure and neuronal circuits' function. Thus, the invention may make the FUP more efficient by determining the best phase, intensity and frequency of the pulse, as well as the best position of the focus or multiple focuses for diagnosis and treatment of the above-mentioned conditions.

The invention can be used for the development of pharmaceuticals. For example, the functional maps of the brain could be created using fMRI before, during, and after a particular pharmaceutical is administered to a patient. If, after administration of the pharmaceutical, the functional reactivity of a certain neuronal circuit becomes similar to that of normal controls, that may be an indicator of the efficacy of the medication.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects illustrative and not restrictive, the scope of the invention being indicated by the appended claims, rather than the foregoing description, and all changes that come within the meaning and range of equivalency of the claims are therefore intended to be embraced therein.

What is claimed is:

1. A method for modifying the electrical currents of a live neuronal circuit within the brain of a mammal, the method comprising the steps of:
   applying a focused ultrasound pulse (FUP) to the live neuronal circuit, where the applied FUP uses a low frequency to disrupt the neuronal circuits or a high frequency to activate the neuronal circuits;
   and monitoring a brain image produced by a brain imaging system during the application of the FUP.

2. The method of claim 1, wherein the mammal is a human.

3. The method of claim 1, further comprising the step of: applying at least one additional FUP to at least one other live neuronal circuit.

4. The method of claim 1, wherein the brain imaging system is selected from the group consisting of a functional magnetic resonance image (fMRI) system; a vector-electroencephalogram (V-EEG), and a positron emission tomograph (PET).

5. The method of claim 1, wherein the step of applying the FUP further comprises the step of applying FUP multiple ultrasound transducers that comprise a non-ferromagnetic material.

6. The method of claim 5, wherein the ultrasound transducers comprise copper.

7. The method of claim 5, wherein there are 300 to 1000 ultrasound transducers.

8. The method of claim 5, wherein the ultrasound transducers are housed in a cap which comprises a non-ferromagnetic material.

9. The method of claim 8, wherein the step of applying FUP further comprises placing the cap on the head of the mammal.

10. The method of claim 8, wherein the cap comprises copper.

11. The method of claim 1, wherein the focus of the FUP is from about 2 to 12 cm into the brain from the exterior of the skull of the mammal.

12. The method of claim 1, wherein the focus of the FUP is at least 2 centimeters into the brain from the exterior of the skull of the mammal.

13. The method of claim 1, wherein the frequency of the FUP is less than 300 Hz.

14. The method of claim 1, wherein the frequency of the FUP is from 500 Hz to 5 MHz.

15. The method of claim 1, further comprising the steps of:
   adjusting the frequency and phase of the FUP to change the focus of the FUP;
   applying a second FUP to the live neuronal circuit.

16. The method of claim 1, further comprising the step of:
running a pre-timed computed tomography (CT) scan to determine bone density and structure of the bone surrounding the brain.

17. The method of claim 1, where the diameter of the focus area of the FUP is approximately 0.5 mm.

18. A method of treating psychiatric, neurological and neuroendocrine disorders in a mammal, the method comprising the steps of:
applying a focused ultrasound pulse (FUP) to the live neuronal circuit, where the applied FUP uses a low frequency to disrupt the neuronal circuits or a high frequency to activate the neuronal circuits;
and monitoring a brain image from a brain imaging system during the application of the FUP.

19. The method of claim 18, wherein the mammal is a human.

20. The method of claim 18, further comprising the step of:
applying at least one additional FUP to at least one other live neuronal circuit.

21. The method of claim 18, wherein the brain imaging system is selected from the group consisting of a functional magnetic resonance image (fMRI) system; a vector -electroencephalogram (V-EEG), and a positron emission tomograph (PET).

22. The method of claim 18, wherein the disorders are selected from the group consisting of Obsessive Compulsive Disorder and its spectrum, Post Traumatic Stress Disorder, Depression, Bipolar Disorder, Social Anxiety Disorder, Psychotic Disorders, Panic Disorder, Ticks, Chronic Pain Syndrome, Insomnia, Chronic Fatigue Syndrome, Insomnia, Stress and Obesity.

23. The method of claim 18, wherein the step of applying FUP further comprises the step of applying FUP via ultrasound transducers that comprise a non-ferromagnetic material.

24. The method of claim 23, wherein the ultrasound transducers comprise copper.

25. The method of claim 23, wherein there are 300 to 1000 ultrasound transducers.

26. The method of claim 23, wherein the ultrasound transducers are housed in a cap which comprises a non-ferromagnetic material.

27. The method of claim 26, wherein the step of applying FUP further comprises placing the cap on the head of the mammal.

28. The method of claim 26, wherein the cap comprises copper.

29. The method of claim 18, wherein the focus of the FUP is 2 or more centimeters into the brain from the exterior of the skull.

30. The method of claim 18, wherein the focus of the FUP is 2-12 cm into the brain from the exterior of the skull.

31. The method of claim 18, wherein the frequency of the FUP is less than 300 Hz.

32. The method of claim 18, wherein the frequency of the FUP is from 500 Hz to 5 MHz.

33. The method of claim 18, further comprising the steps of:
adjusting the frequency and phase of the FUP to change the focus of the FUP;
applying a second FUP to the live neuronal circuit.

34. The method of claim 18, further comprising the step of:
running a pre-timed computed tomography (CT) scan to determine bone density and structure of the bone surrounding the brain.

35. The method of claim 18, further comprising the step of:
administering a pharmaceutical medication to the mammal.

36. The method of claim 18, where the diameter of the focus area of the FUP is approximately 0.5 mm.

* * * * *